United States Patent [19]

Kubouchi

[11] Patent Number: 4,771,791
[45] Date of Patent: Sep. 20, 1988

[54] APPARATUS FOR STORING AND DISPLAYING BODY TEMPERATURE

[75] Inventor: Hideo Kubouchi, Osaka, Japan
[73] Assignee: Benytone Corporation, Osaka, Japan
[21] Appl. No.: 835,696
[22] Filed: Mar. 3, 1986
[51] Int. Cl.⁴ .......................... A61B 5/00; G06F 15/42
[52] U.S. Cl. .................................... 128/736; 128/738; 374/102; 374/170; 364/413.12
[58] Field of Search ................ 374/102, 108; 128/738; 340/588; 364/417

[56] References Cited

U.S. PATENT DOCUMENTS

| | | | |
|---|---|---|---|
| 4,224,949 | 9/1980 | Scott et al. ...................... | 128/738 X |
| 4,367,527 | 1/1983 | Desjacques ...................... | 128/738 X |
| 4,443,851 | 4/1984 | Lin .................................. | 374/186 X |
| 4,447,884 | 5/1984 | Wada .............................. | 374/108 X |
| 4,465,077 | 8/1984 | Schneider ........................ | 128/738 |
| 4,475,158 | 10/1984 | Elias ................................ | 128/738 X |
| 4,487,208 | 12/1984 | Kamens ........................... | 374/170 X |
| 4,488,560 | 12/1984 | Takamura ........................ | 128/738 |
| 4,530,366 | 7/1985 | Nessi et al. ...................... | 128/738 X |

FOREIGN PATENT DOCUMENTS 61-106126  5/1986  Japan .

Primary Examiner—Daniel M. Yasich
Attorney, Agent, or Firm—Armstrong, Nikaido, Marmelstein & Kubovcik

[57] ABSTRACT

A fertility determining apparatus for storing and displaying a measured basal body temperature of a woman and a calendar/clock for generating digital signals representing dates and time. There are separate memory units in the apparatus for storing measured temperature data and data from the calendar/clock. A data processing unit in the apparatus functions to determine whether or not the woman is in a fertile period based upon data stored within the apparatus and the corresponding basal temperature.

7 Claims, 4 Drawing Sheets 4,771,791

APPARATUS FOR STORING AND DISPLAYING BODY TEMPERATURE

BACKGROUND OF THE INVENTION

1. Field of the Invention

The present invention relates to an apparatus for storing and displaying body temperature which is capable of measuring the body temperature of a human and storing its value. More particularly, the invention pertains to an apparatus for storing and displaying body temperature which is improved so that it can measure the basal body temperature of a woman and judge whether or not that woman is in a fertile period.

2. Description of the Prior Art

Heretofore, a basal body temperature method has been used to determine whether a woman is in her fertile period or not. This method, however, is irksome in that it requires the woman to plot the measured value on a graph each time her temperature is taken. In addition, time-consuming calculations are required to forecast the next fertile period on the basis of the above-mentioned values on the graph.

Basal body temperature is also used for the diagnosis of women's diseases. In this case, however, the gynecologist has to take into account the possibility of the patient misreading the thermometer.

SUMMARY OF THE INVENTION

In view of the above-described problems, it is a primary object of the present invention to provide an apparatus for storing and displaying body temperature which is improved so that it can record and display basal body temperature in a simple manner. Another object of the invention is to provide an apparatus for storing and displaying body temperature which makes it possible to see at a glance whether a woman is in a fertile period.

To these, the present invention provides an apparatus for storing and displaying body temperature which comprises a calender/clock which serves as a calender, a clinical thermometer for measuring body temperature and producing a digital signal corresponding to that temperature, a memory for storing data representing the temperature measured by the clinical thermometer, a processing circuit for judging and predicting whether a woman is impregnable on the basis of the data obtained by the clinical thermometer and Mr. Ogino's data, and a display means for displaying the output of the calender/clock, the output of the clinical thermometer, and the estimated basal body temperature and estimated fertile period which are information processed by the processing circuit.

DESCRIPTION OF THE PREFERRED EMBODIMENTS

Figure 1:
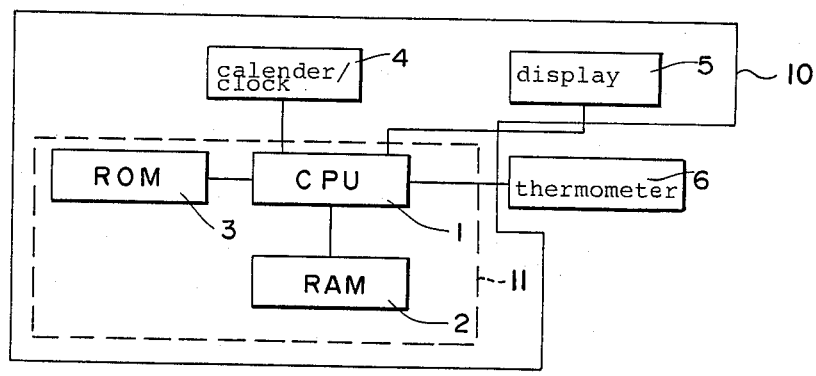
FIG. 1 is a block diagram of an embodiment of the present invention, showing its electrical configuration.

Referring first to FIG. 1, the apparatus 10 of the present invention has a calender/clock 4 which functions as a calender, i.e., it sends digital signals representing the date and time to a CPU (central processing unit) 1 of a control unit 11. A ROM (read-only memory) 3 is to store data expressing the theory established by Mr. Ogino (Shinkyo Sankagaku (new obstetrics and gynecology) by Shozaburo Sodeki and Hiroshi Kawakami published 1963 by Kanehara Shuppan Kabushiki Kaisha); as well as to store a program used for operating the CPU 1. A RAM (random-access memory) 2 stores the data sent from a clinical thermometer 6 and the calender/clock 4. A display 5 displays the data which are produced by the CPU 1 and the clinical thermometer 6, as well as the date and time output by the calender clock 4.

Figure 2:
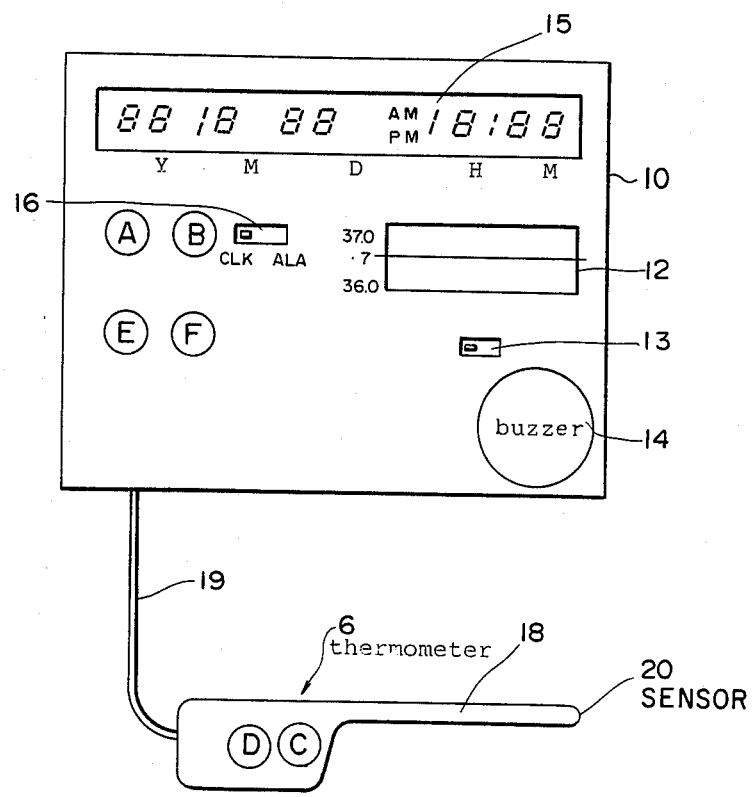
FIG. 2 is a schematic front view of the apparatus for storing and displaying body temperature according to the present invention.

Referring next to FIG. 2, a display section 15 and a display section 12 together correspond to the display 5 of FIG. 1. The display section 15 acts as a calender, i.e., it displays the current date and time. The display section 12 displays temperatures in the form of a bar graph with dates along the abscissa and temperatures along the ordinate. The display of the calender by the display section 15 can be changed over to a wake-up time by means of a switch 16. A switch 13 turns on and off the display of the display section 12. A piezo-electric buzzer 14 generates a wake-up alarm, and also produces an operation confirmation sound. The calender/clock of the display section 15 and the contents of the display section 12 are adjusted by a pushbutton A. The wake-up time is adjusted by a pushbutton B. Pushbuttons E and F are both employed when reading out the contents of the RAM shown in FIG. 1 or when displaying past and future basal body temperatures, as well as estimated fertile days. Pushbutton E is used for moving dates backward and pushbutton F for moving them forward.

The clinical thermometer 6, as shown in FIG. 2, has a sensor 20, a temperature-measuring body 18, a pushbutton C, a pushbutton D, and a lead wire 19. The clinical thermometer 6 measures temperature by its sensor 20 and transmits a digital signal corresponding to the measured temperature data to the CPU 1 through the lead wire 19. The pushbutton D is used when starting the operation of the apparatus and when writing data in the RAM 2. The pushbutton C acts as a switch for confirming that the operator is awake, and is operated when the wake-up buzzer is stopped. Pushbutton C is necessary because the basal body temperature must be taken while lying quietly in bed immediately after waking in the morning.

Figure 3:
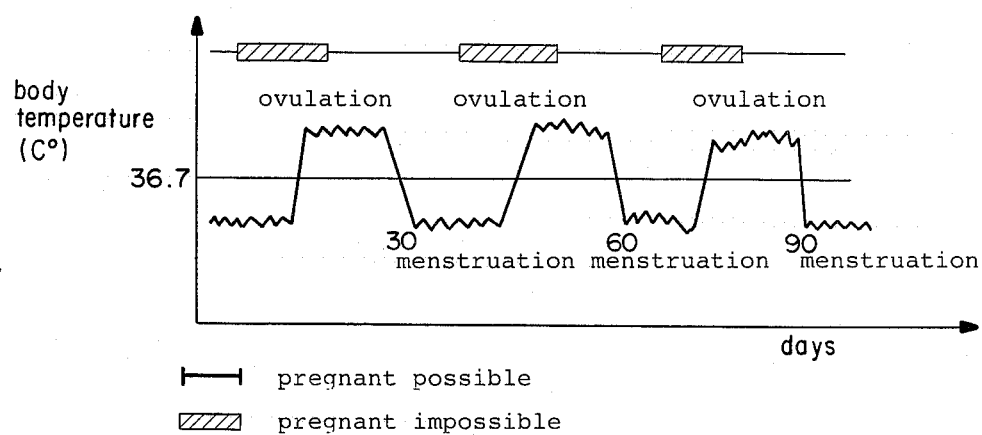
FIG. 3 is a graph showing daily changes in body temperatures.

FIG. 3 shows a graph of the basal body temperature of a woman, showing how her temperature fluctuates over about 90 days. The menstrual cycle of this woman can be seen from the graph to be about 30 days long.

Temperature rises when ovulation occurs, and falls when menstruation commences. The basal body temperature of a woman can be slightly above or below normal, depending on the individual. However, if a temperature of 36.7° C., is taken as standard, a normal woman has a repetitive two-phase cycle in which higher temperatures are referred to as the high-temperature phase, and the lower temperatures of the cycle are referred to as the low-temperature phase. Since ova and spermatozoa can survive for a certain period, a woman can become pregnant during several days around ovulation.

Figure 4:
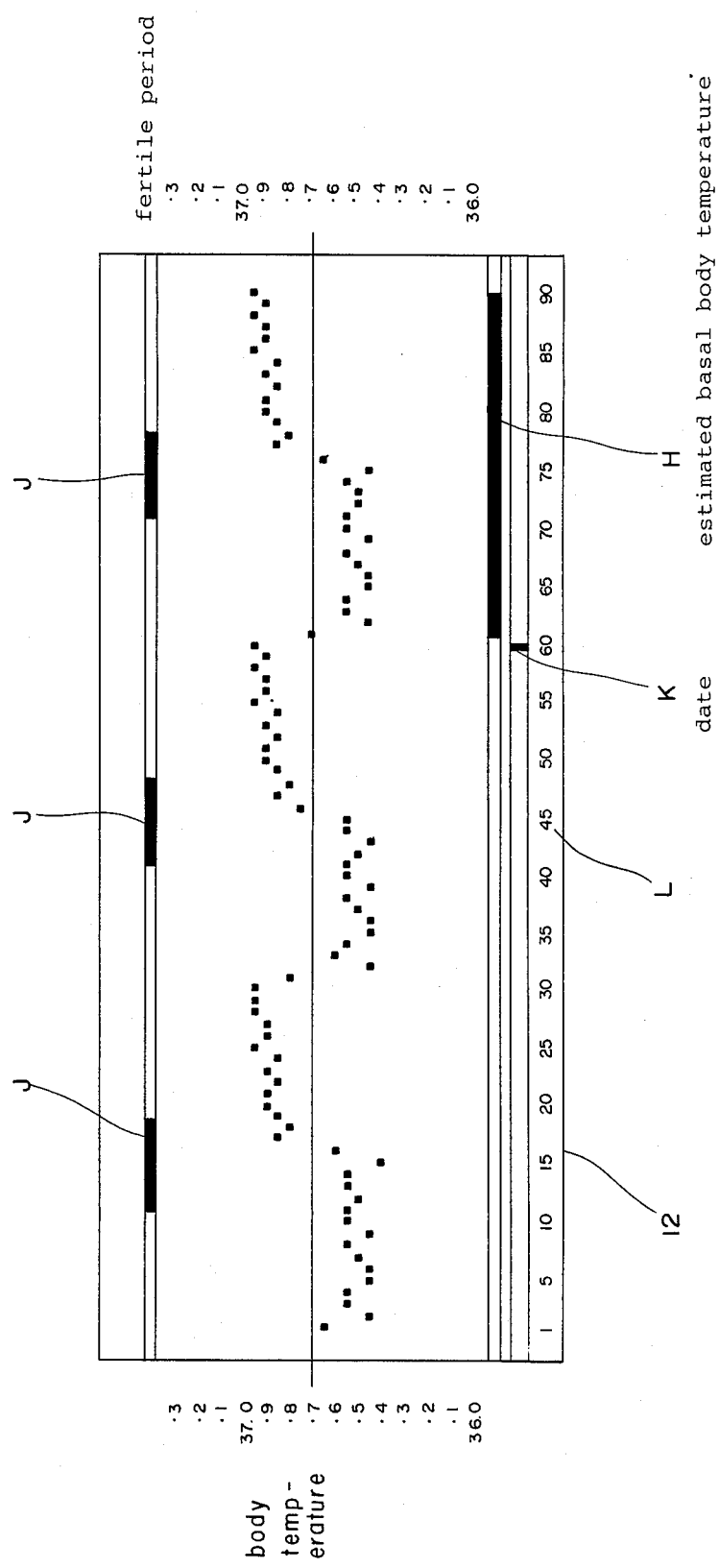
FIG. 4 is an enlarged detail view of the display section 12.

FIG. 4 is a graph of basal body temperatures over a period of 90 days, which are sequentially indicated day by day. The temperatures for the 60 days in the left part of the Figure represent those which were actually measured. On the other hand, those for the 30 days on the right are the estimated results calculated by the processing circuit on the basis of the data on basal body temperatures which had been taken for 60 the days shown on the left of the graph, and before that period. The temperatures in the portion with an indicator H in the display section 12 are estimated. An indicator J indicates the fertile periods and an estimated fertile period which is calculated on the basis of the data on measured basal body temperatures and the data representing the Ogino method. The date displayed by the display section 15 is indicated by an indicator K in the display section 12.

The operation of the apparatus will be described hereinunder with reference to the flowchart of FIG. 5.

Figure 5:
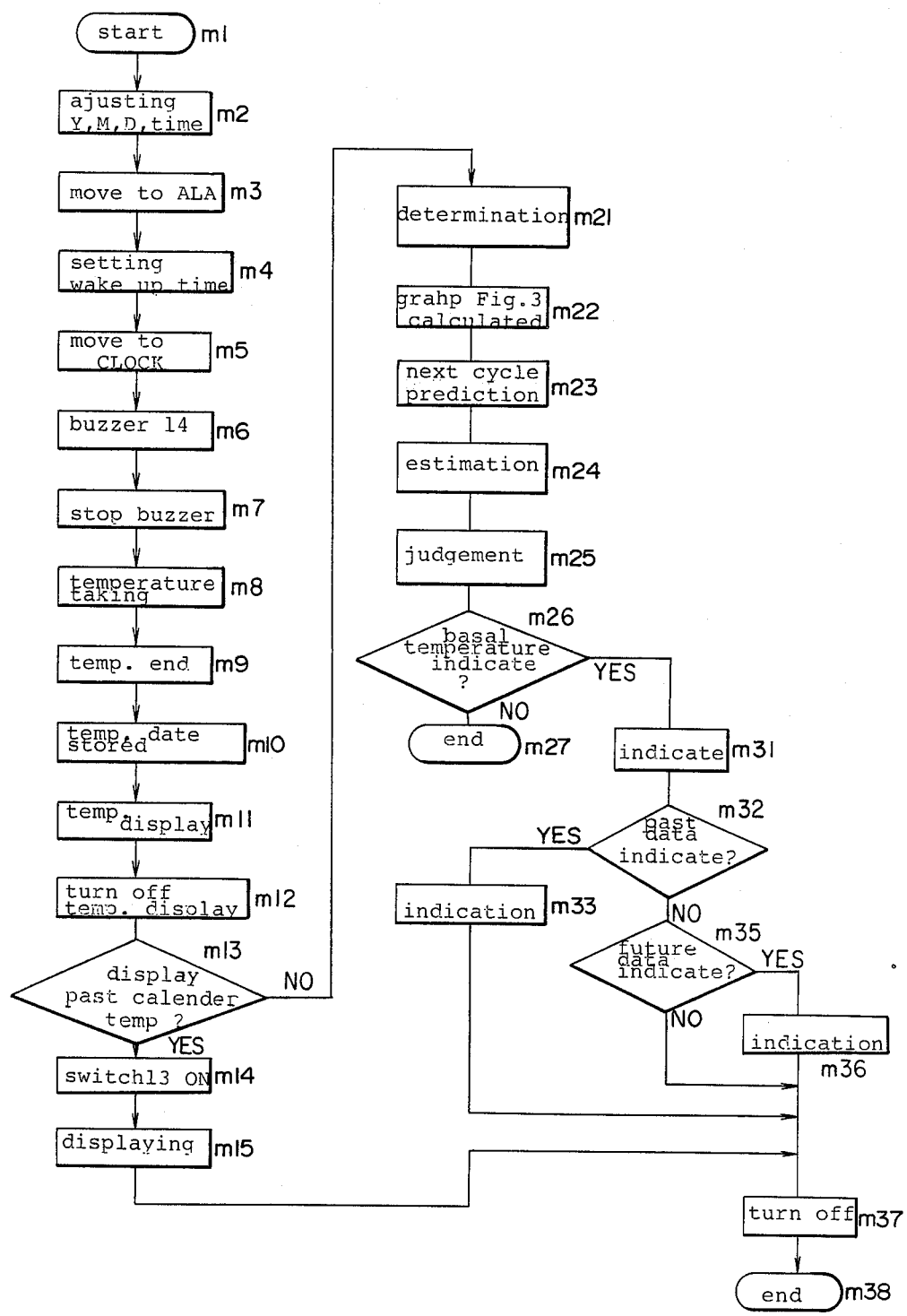
FIG. 5 is a flowchart used for explaining the operation of an embodiment of the present invention.

In FIG. 5, the apparatus is started in Step m1, and the process proceeds to Step m2. In Step m2, the year, month, day, and time, which are displayed in the display section 15, are adjusted by pressing pushbutton A shown in FIG. 2. Thereafter, in Step m3, the switch 16 is moved to ALA so that the display section 15 displays the time at which an alarm is set. In Step m4, a wake-up time is selected by pressing pushbutton B. In Step m5, the switch 16 is moved to CLOCK so that the display section 15 displays the date.

In Step m6, the piezo-electric buzzer 14 goes off at the wake-up time the next morning, which is set in the above-mentioned manner, making a wake-up noise. In Step m7, the buzzer is then stopped by pressing pushbutton C. Subsequently, in Step m8, temperature taking is started by pressing pushbutton D while placing the sensor 20 of the clinical thermometer 6 in the mouth. In Step m9, the piezo-electric buzzer 14 goes off when the temperature taking is completed, indicating that the temperature has been taken. The process proceeds to Step m10 in which the value of the temperature as well as the calender date at that time are stored in the RAM 2 by pressing pushbutton D. In addition, the indicator sound from the buzzer is stopped in Step m9. The thus-obtained temperature is displayed in the display section 12 in Step m11. For example, a display section 12 such as shown in FIG. 4 displays the basal body temperatures for 90 days. In this way, a temperature graph is sequentially drawn day by day.

Subsequently, the switch 13 is moved to OFF in Step m12, so as to turn off the display of the temperature by the display section 12.

The process then proceeds to Step m13 in which it is determined whether to display past calender dates and corresponding temperatures. If past dates and temperatures are to be displayed, Step m14 is executed in which the switch 13 is set to ON. In Step m15, the individual data items are displayed in the display sections 15 and 12. The contents of the displays of the display sections 15 and 12 at that time are past dates and times and the corresponding basal body temperatures, respectively.

In this way, it is possible to make the past calender data and the corresponding basal body temperatures into a graph and display them on the display section 12, so that it is not necessary to manually plot them on graph paper. To determine whether that woman is in her fertile period on the basis of the past calender content and the data representing the corresponding temperatures obtained in Step m13, the process proceeds to Step m21. In Step m21, a calculation is done to determine whether the measured basal temperature is higher or lower than the mean basal body temperature of 36.7° C. shown in FIG. 3. The mean basal body temperature is obtained from the mean value of the temperature data, since it varies from individual to individual. The cycle of the temperatures shown in the graph of FIG. 3 is then calculated in Step m22, and the next cycle is predicted in Step m23. If a first cycle starts on March 31, for example, it is calculated that the second cycle will begin on April 30. In Step m24, the dates of the high-temperature phase and the low-temperature phase are estimated; and in Step m25, a judgment or determination is made as to whether that woman is in her fertile period based on the OGINO method. If it is decided that she is fertile, the indicator J in the display section 12 flashes.

The determination as to whether the woman is in her fertile period can be done, since data expressing the Ogino method is already stored in the ROM 3.

Subsequently, if it is decided in Step m27 not to display the past and future basal body temperatures, the process proceeds to Step m27. Otherwise, Step m31 is then executed.

In Step m31, the temperatures are displayed in the display section 12 by moving the switch 13 to ON. If it is decided to display the past data in Step m32, Step m33 is executed in which the past data, represented by the output of the calender/clock 4 of the display section 15 and the dates and basal body temperatures of the display section 12, is displayed by pressing the pushbutton E of FIG. 2. The contents of the display can be changed, and the data corresponding to any desired date and its surroundings can be selected by pressing pushbutton E.

To know future basal body temperatures and future fertile periods, the process proceeds from Step m35 to Step m36.

In Step m36, the estimated future basal body temperatures, represented by the output of the calender/clock 4 as well as by the dates and basal body temperatures 12, are displayed by the display sections 15 and 12, respectively, by pressing pushbutton F of FIG. 2. The indicator H is attached to the estimated temperatures, and the indicator J is given to the estimated fertile periods.

If it is not necessary to display the future data, the display of the display section 12 is changed to the that of temperature in Step m37, by moving the switch 13 to OFF. The contents of the display section 15 may alternatively be displayed by the display section 12. A bar graph may be employed in place of the graph such as shown in FIGS. 3 and 4.

According to the present invention, the basal body temperatures can be automatically and sequentially made into a graph day by day, by means of which it is possible to estimate future fertile periods or sterile periods and to discover pregnancy and diseases specific to women at an early stage.

In addition, the display section 12 of the apparatus of the invention may alternatively be used such as to display biorhythms. The application of the apparatus of the invention is not limited to women, and it may also serve as a health care instrument for anybody including the sick and infants.

The stored data may be output by a printer such as to obtain hard copy, and input into a computer so that it can be used for medical analysis.

What is claimed is:

1. An apparatus for storing and displaying body temperature, said apparatus comprising:
   a calendar/clock generates digital signals representing date and time;
   a clinical thermometer measures basal body temperature for a preselected time period and produces a digital signal corresponding to said temperature;
   a first memory unit stores the data output by said clinical thermometer and said calendar/clock;
   a second memory unit stores data for determining fertility and said second memory unit contains stored computer programs;
   a processing unit determines fertility based upon the data from said clinical thermometer stored in said first memory unit and the data on fertility stored in said second memory unit using said computer programs stored in said second memory unit, said processing unit also predicting future fertility based upon the data from said clinical thermometer and said data on fertility using said computer programs; and
   a display means displays the output of said calendar/clock, the output of said clinical thermometer and the fertility determined by said processing unit.

2. An apparatus for storing and displaying body temperature according to claim 1 further comprising an alarm means for generating a wake up alarm, a means to activate said alarm means based on said calendar/clock, a means to control said display means and a means for setting the date and time of said calendar/clock.

3. An apparatus for storing and displaying body temperature according to claim 1, wherein said clinical thermometer further comprises a sensor, a body, and an operational means for operating said clinical thermometer.

4. An apparatus for storing and displaying body temperature according to claim 1, wherein said display means displays temperature in the form of a bar graph with dates along the abscissa and temperatures along the ordinate.

5. An apparatus for storing and displaying body temperature, said apparatus comprising:
   a clinical thermometer measures body temperature for a predetermined time period and generates a digital signal corresponding to said temperature;
   a calendar/clock generates a digtial signal representing a date and a time, said calendar/clock generating a digital signal representing a wake-up time for generating a wake-up alarm;
   a memory unit connected to said calendar/clock and said clinical thermometer, said memory unit stores the temperature from said clinical thermometer, the date and times from said calendar/clock and stores data on fertility;
   a processing unit determines current fertility and future fertility based on data stored in the memory unit on the temperature from said clinical thermometer, data on fertility and date and time from said calendar/clock;
   display means connected to said memory unit, said display means selectively displays the temperature of said clinical thermometer stored in said memory unit, the date and times of said calendar/clock stored in said memory unit and current and future fertility;
   activation means to activate said alarm means to generate said wake-up alarm from the wake-up time of the calendar/clock stored in said memory unit;
   control means to control said display means to selectively display said date and time, said wake-up time, current and future fertility, said temperature and to turn said display means on and off; and
   setting means for setting a current date and time of said calendar/clock and for setting said wake-up time.

6. An apparatus for storing and displaying body temperature as claimed in claim 5, wherein said clinical thermometer further comprises a sensor, a body, and control means for controlling said clinical thermometer.

7. An apparatus for storing and displaying body temperature, said apparatus comprising;
   a calendar/clock functioning as a calendar;
   a clinical thermometer measures a woman's basal body temperature and produces a digital signal corresponding to said temperature;
   a memory unit for storing data output by said clinical thermometer;
   a processing circuit determines whether a woman is fertile on the basis of the data from said clinical thermometer and data stored in the memory unit and predicts future fertility from data stored in the memory unit expressing Mr. Ogino's theory;
   a display means for displaying output of said calendar/clock, the output of said clinical thermometer, and the data processed by said processing circuit, said display means comprising a first display section acting as a calendar/clock to display the current date and time, and a second display section for displaying the temperature in a form of bar graph;
   a switch means comprising a first switch by which the display of the calendar by the first display section can be changed over to a wake-up time, when moving the first switch to a first position, the first display section can display the time at which an alarm is set, and when moving the first switch to a second position, the first display section can display the date, and a second switch by which the display of the second display section can be turned ON or OFF, when setting the second switch ON, the past calendar dates and temperatures corresponding to past calendar dates can be displayed, and when setting the second switch OFF, the display of the temperature by the second display is turned OFF; and
   a push button means comprising a first push button for adjusting the calendar/clock of the first display section and the contents of the second display section, a second push button for adjusting the wake-up time, a third push button for stopping a buzzer to confirm that a user is awake, a fourth push button for starting the operation of the apparatus and for writing data in the memory unit, a fifth push button for moving dates backward as well as to read out the contents in the memory unit and the past basal body temperature, and a sixth push button for moving date forward as well as to display the future basal body temperatures and the estimated fertile days.

* * * * *